(12) United States Patent
Hamada et al.

(10) Patent No.: US 7,781,609 B2
(45) Date of Patent: **\*Aug. 24, 2010**

(54) PROCESS FOR PRODUCING OPTICALLY ACTIVE β-HYDROXY-α-AMINOCARBOXYLIC ACID DERIVATIVE

(75) Inventors: Yasumasa Hamada, Chiba (JP); Kazuishi Makino, Chiba (JP)

(73) Assignee: Nissan Chemical Industries, Ltd., Tokyo (JP)

( \* ) Notice: Subject to any disclaimer, the term of this patent is extended or adjusted under 35 U.S.C. 154(b) by 410 days.

This patent is subject to a terminal disclaimer.

(21) Appl. No.: 11/795,035
(22) PCT Filed: Jan. 12, 2006
(86) PCT No.: PCT/JP2006/000275
§ 371 (c)(1), (2), (4) Date: Jul. 12, 2007
(87) PCT Pub. No.: WO2006/075651
PCT Pub. Date: Jul. 20, 2006

(65) Prior Publication Data
US 2008/0139825 A1 Jun. 12, 2008

(30) Foreign Application Priority Data
Jan. 12, 2005 (JP) .............................. 2005-005366

(51) Int. Cl.
*C07C 229/00* (2006.01)
(52) U.S. Cl. ........................................ 560/42; 560/170
(58) Field of Classification Search ................. 560/42, 560/170, 564; 558/410
See application file for complete search history.

(56) References Cited

U.S. PATENT DOCUMENTS 5,565,594 A \* 10/1996 Spindler et al. ................ 556/28
2006/0167300 A1\* 7/2006 Hamada et al. ............. 558/410

FOREIGN PATENT DOCUMENTS

EP 0 612 758 A1 8/1994

(Continued)

OTHER PUBLICATIONS

R. Noyori et al., "Stereoselective Hydrogenation via Dynamic Kinetic Resolution," *J. Am. Chem. Soc.*, 1989, vol. 111, pp. 9134-9135.

(Continued)

*Primary Examiner*—Taylor Victor Oh
(74) *Attorney, Agent, or Firm*—Oliff & Berridge, PLC

(57) ABSTRACT

There is provided a process for efficiently producing an anti form of an optically active β-hydroxy-α-aminocarboxylic acid derivative that is useful as an intermediate for pharmaceuticals and agrochemicals. The process for producing optically active β-hydroxy-α-aminocarboxylic acid derivative of formula (2) or (3)

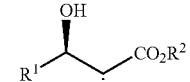

(2)

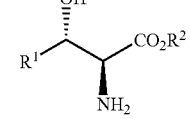

(3)

therein $R^1$ is substituted or unsubstituted $C_{1-20}$ alkyl group, or substituted or unsubstituted $C_{4-12}$ aromatic group, $R^2$ is substituted or unsubstituted $C_{1-20}$ alkyl group, or substituted or unsubstituted $C_{4-12}$ aromatic group, comprising subjecting an α-aminoacyl acetic acid ester compound of formula (1)

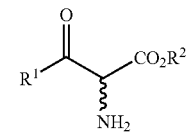

(1)

wherein $R^1$ and $R^2$ have the same meaning as the above, to hydrogenation by catalytic asymmetric hydrogenation in the presence of an acid by using as a catalyst a rhodium complex containing as a ligand an optically active compound of formula (4), (4') or (5)

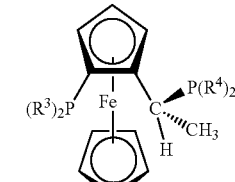

(4)

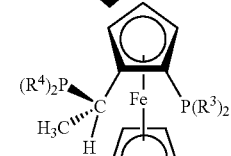

(4')

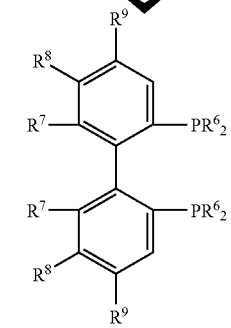

(5)

characterized in that the hydrogenation is conducted in the presence of an acetic acid salt.

13 Claims, No Drawings

FOREIGN PATENT DOCUMENTS

| | | |
|---|---|---|
| JP | A-02-172956 | 7/1990 |
| JP | A-06-080617 | 3/1994 |
| JP | A-07-118282 | 5/1995 |
| WO | WO 2005/005371 A1 | 1/2005 |

OTHER PUBLICATIONS

Ulrich Schmidt et al., "Total Synthesis of the Biphenomycins;" *Synthesis*, 1992, pp. 1248-1254.

Ryoji Noyori et al., *Asymmetric Catalysis in Organic Synthesis*, (1994), pp. 1-95.

Olivier Labeeuw et al., "Total synthesis of sulfobacin A through dynamic kinetic resolution of a racemic β-keto-α- amino ester hydrochloride," *Tetrahedron: Asymmetry*, 2004, vol. 15, No. 12, pp. 1899-1908, pp. 1901 Scheme 5, pp. 1904-1905.

J. P. Genet, et al., "Asymmetric Synthesis. Practical Production of D and L Threonine. Dynamic Kenetic Resolution in Rhodium and Ruthenium Catalyzed Hydrogenation of 2-Acylamino-3-Oxobutyrates," *Tetrahedron: Asymmetry*, 1991, vol. 2, No. 7, pp. 555-567.

Ryoichi Kuwano et al., Catalytic Ayrnmetric Synthesis of β-Hydroxy-α-amino Acids: Highly Enantioselective Hydrogenation of β-Oxy-α-acetamidoacrylates, *Journal of Organic Chemistry*, 1998, vol. 63, No. 10, pp. 3499-3503.

* cited by examiner

PROCESS FOR PRODUCING OPTICALLY ACTIVE β-HYDROXY-α-AMINOCARBOXYLIC ACID DERIVATIVE

TECHNICAL FIELD

The present invention relates to a process for producing optically active β-hydroxy-α-aminocarboxylic acid derivative that is useful as an intermediate for pharmaceuticals and agrochemicals.

BACKGROUND ART

Optically active β-hydroxy-α-aminocarboxylic acid derivatives are important intermediates for compounds useful as several fine chemical materials represented by physiologically active substances such as pharmaceuticals and agrochemicals, etc.

As a process for producing optically active β-hydroxy-α-aminocarboxylic acid derivative, a process is known in which a racemic α-aminoacyl acetic acid ester compound is subjected to asymmetric hydrogenation by catalytic asymmetric hydrogenation with ruthenium-optically active phosphine complex catalyst to produce syn-selectively an optically active β-hydroxy-α-aminocarboxylic acid derivative (see, for example, Non-patent Documents 1 and 2, and Patent Document 1).

On the other hand, asymmetric hydrogenation with a transition metal catalyst of olefins, ketones and imines has been known well (see, for example, Non-patent Document 3).

In addition, it is reported an anti-selective process for producing 3-(3,4-dihydroxyphenyl) serine derivative being one of β-hydroxy-α-aminocarboxylic acid derivatives by asymmetric hydrogenation with a rhodium catalyst containing (+)-DIOP as an asymmetric ligand (see, for example Patent Document 2).

Further, an example of asymmetric hydrogenation with a rhodium complex containing a specific ferrocene derivative as a ligand is known (see, for example Patent Document 3).

However, hydrogenation in the presence of an acetic acid salt has not been known.

Patent Document 1: JP-A-6-80617 (1994)

Patent Document 2: JP-A-2-172956 (1990)

Patent Document 3: EP-A-0612758 (1994)

Non-patent Document 1: J. Am. Chem. Soc., 1989, 111, p. 9134-9135

Non-patent Document 2: SYNTHESIS, 1992, p. 1248-1254

Non-patent Document 3: R. Noyori ed. Asymmetric Catalysis in Organic Synthesis, (1994) Jhon Wiley & Sons, Inc, New York

DISCLOSURE OF INVENTION

Problem to be Solved by the Invention

The processes disclosed in Non-patent Documents 1 and 2 and Patent Document 1 are excellent as processes for selectively producing the syn form of optically active β-hydroxy-α-aminocarboxylic acid derivative.

However, as these processes cannot directly produce the anti form of optically active β-hydroxy-α-aminocarboxylic acid derivative, it was required to produce the syn form once and revert the configuration of the one side in order to produce the anti form. In addition, the process disclosed in Patent Document 2 can produce an anti form in a high selectivity but the optical yield thereof is as low as 12.3% ee.

Means for Solving the Problem

The present inventors eagerly investigated as to processes for selectively producing the anti form of optically active β-hydroxy-α-aminocarboxylic acid derivative. As a result of it, they found that the anti form of optically active β-hydroxy-α-aminocarboxylic acid derivative can be easily obtained in an efficient manner by performing asymmetric hydrogenation in the presence of an acetic acid salt when the hydrogenation is carried out by use of a rhodium catalyst containing a specific asymmetric ligand in the presence of an acid, and they completed the present invention.

That is, the present invention pertains to the followings:

1. A process for producing optically active β-hydroxy-α-aminocarboxylic acid derivative of formula (2) or (3)

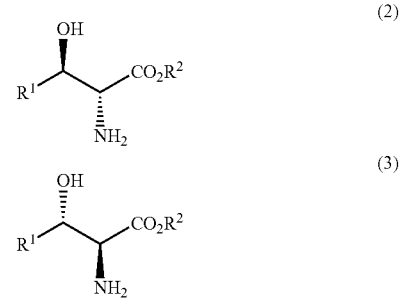

wherein $R^1$ is $C_{1-20}$ alkyl group [the $C_{1-20}$ alkyl group may be arbitrarily substituted with $C_{4-12}$ aromatic group (the aromatic group may be arbitrarily substituted with halogen atom, $C_{1-6}$ alkyl group, $C_{1-6}$ alkoxy group, $C_{1-6}$ alkoxycarbonyl group, $C_{1-6}$ alkylcarbonyloxy group or $CONR^a R^b$ wherein $R^a$ and $R^b$ are independently of each other are hydrogen atom or $C_{1-6}$ alkyl group), Ciba alkoxy group, $C_{1-6}$ alkoxycarbonyl group or $CONR^a R^b$ wherein $R^a$ and $R^b$ are independently of each other are hydrogen atom or $C_{1-6}$ alkyl group], or $C_{4-12}$ aromatic group [the aromatic group may be arbitrarily substituted with halogen atom, $C_{1-6}$ alkyl group, $C_{1-6}$ alkoxy group, $C_{1-6}$ alkoxycarbonyl group, $C_{1-6}$ alkylcarbonyloxy group (the $C_{1-6}$ alkyl group, $C_{1-6}$ alkoxy group, $C_{1-6}$ alkoxycarbonyl group and $C_{1-6}$ alkylcarbonyloxy group may be arbitrarily substituted with $C_{4-12}$ aromatic group (the aromatic group may be arbitrarily substituted with halogen atom)) or $CONR^a R^b$ wherein $R^a$ and $R^b$ are independently of each other are hydrogen atom or $C_{1-6}$ alkyl group], $R^2$ is $C_{1-20}$ alkyl group [the $C_{1-20}$ alkyl group may be arbitrarily substituted with $C_{4-12}$ aromatic group (the aromatic group may be arbitrarily substituted with halogen atom, $C_{1-6}$ alkyl group, $C_{1-6}$ alkoxy group, $C_{1-6}$ alkoxycarbonyl group, $C_{1-6}$ alkylcarbonyloxy group or $CONR^a R^b$ wherein $R^a$ and $R^b$ are independently of each other are hydrogen atom or $C_{1-6}$ alkyl group), $C_{1-6}$ alkoxy group, $C_{1-6}$ alkoxycarbonyl group or $CONR^a R^b$ wherein $R^a$ and $R^b$ are independently of each other are hydrogen atom or $C_{1-6}$ alkyl group], or $C_{4-12}$ aromatic group [the aromatic group may be arbitrarily substituted with halogen atom, $C_{1-6}$ alkyl group, $C_{1-6}$ alkoxy group, $C_{1-6}$ alkoxycarbonyl group, $C_{1-6}$ alkylcarbonyloxy group or $CONR^aR^b$ wherein $R^a$ and $R^b$ are independently of each other are hydrogen atom or $C_{1-6}$ alkyl group], comprising subjecting an α-aminoacyl acetic acid ester compound of formula (1)

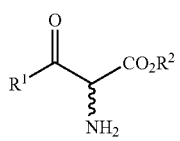
(1)

wherein $R^1$ and $R^2$ have the same meaning as the above, to hydrogenation by catalytic asymmetric hydrogenation in the presence of an acid by using as a catalyst a rhodium complex containing as a ligand an optically active compound of formula (4), (4') or (5)

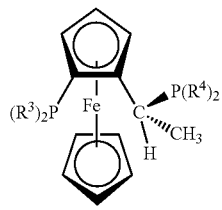
(4)

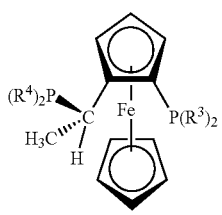
(4')

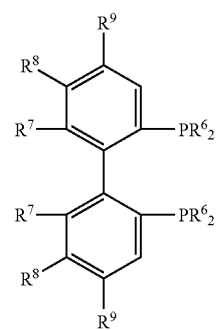
(5)

wherein $R^3$ and $R^4$ are independently of each other are phenyl group [the phenyl group may be arbitrarily substituted with $C_{1-4}$ alkyl group or $C_{1-4}$ alkoxy group (the $C_{1-4}$ alkyl group and $C_{1-4}$ alkoxy group may be arbitrarily substituted with fluorine atom)], $C_{1-7}$ alkyl group or 2-furyl group, $R^6$ is phenyl group, naphthyl group (the phenyl group and naphthyl group may be arbitrarily substituted with $C_{1-6}$ alkyl group or $C_{1-6}$ alkoxy group), cyclopentyl group or cyclohexyl group, $R^7$ is methyl group or methoxy group, $R^8$ is hydrogen atom, methyl group, methoxy group or chlorine atom, $R^9$ is hydrogen atom, methyl group, methoxy group, dimethylamino group or diethylamino group, and absolute configuration is either S or R, characterized in that the hydrogenation is conducted in the presence of an acetic acid salt;

2. The process for producing optically active β-hydroxy-α-aminocarboxylic acid derivative as set forth in 1., wherein the ligand of the rhodium complex is the optically active compound of formula (4) or (4');

3. The process for producing optically active β-hydroxy-α-aminocarboxylic acid derivative as set forth in 2., wherein $R^3$ is phenyl group, cyclohexyl group, 2-furyl group, 3,5-bistrifluoromethylphenyl group, 4-trifluoromethylphenyl group or 3,5-dimethyl-4-methoxyphenyl group, and $R^4$ is tert-butyl group, cyclohexyl group, phenyl group or 3,5-dimethylphenyl group;

4. The process for producing optically active β-hydroxy-α-aminocarboxylic acid derivative as set forth in 3., wherein the ligand is (R)-(−)-1-[(S)-2-(bis(4-trifluoromethylphenyl)phosphino)ferrocenyl]ethyl-di-tert-butylphosphine, (R)-(−)-1-[(S)-2-(di(3,5-bistrifluoromethylphenyl)phosphino)ferrocenyl]ethyl-dicyclohexylphosphine, (R)-(−)-1-[(S)-2-(di(3,5-bistrifluoromethylphenyl)phosphino)ferrocenyl]ethyl-di(3,5-dimethylphenyl)phosphine, (R)-(−)-1-[(S)-2-(dicyclohexylphosphino)ferrocenyl]ethyl-di-tert-butylphosphine, (R)-(−)-1-[(S)-2-(dicyclohexylphosphino)ferrocenyl]ethyl-dicyclohexylphosphine, (S)-(+)-1-[(R)-2-(dicyclohexylphosphino)ferrocenyl]ethyl-dicyclohexylphosphine, (S)-(+)-1-[(R)-2-(dicyclohexylphosphino)ferrocenyl]ethyl-diphenylphosphine, (R)-(−)-1-[(S)-2-(bis(3,5-dimethyl-4-methoxyphenyl)phosphino)ferrocenyl]ethyl-dicyclohexylphosphine, (S)-(+)-1-[(R)-2-(di-2-furylphosphino)ferrocenyl]ethyl-di(3,5-dimethylphenyl)phosphine, (R)-(−)-1-[(S)-2-(diphenylphosphino)ferrocenyl]ethyl-di-tert-butylphosphine, (S)-(+)-1-[(R)-2-(diphenylphosphino)ferrocenyl]ethyl-di-tert-butylphosphine, (R)-(−)-1-[(R)-2-(diphenylphosphino)ferrocenyl]ethyl-dicyclohexylphosphine, (S)-(+)-1-[(R)-2-(diphenylphosphino)ferrocenyl]ethyl-dicyclohexylphosphine, (R)-(−)-1-[(S)-2-(dicyclohexylphosphino)ferrocenyl]ethyl-diphenylphosphine or (R)-(−)-1-[(S)-2-(diphenylphosphino)ferrocenyl]ethyl-di(3,5-dimethylphenyl)phosphine;

5. The process for producing optically active β-hydroxy-α-aminocarboxylic acid derivative as set forth in 4., wherein the ligand is (R)-(−)-1-[(S)-2-(diphenylphosphino)ferrocenyl]ethyl-di-tert-butylphosphine;

6. The process for producing optically active β-hydroxy-α-aminocarboxylic acid derivative as set forth in 1., wherein the ligand of the rhodium complex is the optically active compound of formula (5);

7. The process for producing optically active β-hydroxy-α-aminocarboxylic acid derivative as set forth in 6., wherein $R^6$ is cyclohexyl group, phenyl group, 4-methylphenyl group, 4-methoxyphenyl group or 4-tert-butylphenyl group, $R^7$ is methyl group or methoxy group, $R^8$ is hydrogen atom or methoxy group, and $R^9$ is hydrogen atom, methyl group or dimethylamino group;

8. The process for producing optically active β-hydroxy-α-aminocarboxylic acid derivative as set forth in 7., wherein the ligand is 2,2'-dimethyl-6,6'-bis(diphenylphosphino)-1,1'-biphenyl, 2,2'-dimethyl-6,6'-bis(dicyclohexylphosphino)-1,1'-biphenyl, 2,2'-dimethyl-4,4'-bis(dimethylamino)-6,6'-bis(diphenylphosphino)-1,1'-biphenyl, 2,2',4,4'-tetramethyl-6,6'-bis(diphenylphosphino)-1,1'-biphenyl, 2,2'-dimethoxy-6,6'-bis(diphenylphosphino)-1,1'-biphenyl, 2,2',3,3'-tetramethoxy-6,6'-bis(diphenylphosphino)-1,1'-biphenyl, 2,2',4,4'-tetramethyl-3,3'-dimethoxy-6,6'-bis(diphenylphosphino)-1,1'-biphenyl, 2,2'-dimethyl-6,6'-bis(di-4-methylphenylphosphino)-1,1'-biphenyl, 2,2'-dimethyl-6,6'-bis(di-4-tert-butylphenylphosphino)-1,1'-biphenyl or 2,2',4,4'-tetramethyl-3,3'-dimethoxy-6,6'-bis(di-4-methoxyphenylphosphino)-1,1'-biphenyl;

9. The process for producing optically active β-hydroxy-α-aminocarboxylic acid derivative as set forth in 8., wherein the ligand is 2,2'-dimethoxy-6,6'-bis(diphenylphosphino)-1,1'-biphenyl;

10. The process for producing optically active β-hydroxy-α-aminocarboxylic acid derivative as set forth in any one of 1. to 9., wherein the acid is a strong acid;

11. The process for producing optically active β-hydroxy-α-aminocarboxylic acid derivative as set forth in any one of 1. to 10., wherein acetic acid is used as a solvent;

12. The process for producing optically active β-hydroxy-α-aminocarboxylic acid derivative as set forth in any one of 1. to 11., wherein the acetic acid salt is sodium acetate;

13. The process for producing optically active βhydroxy-α-aminocarboxylic acid derivative as set forth in any one of 1. to 12., wherein the rhodium complex is a compound prepared from $[RhCl(nbd)]_2$ or $[Rh(nbd)_2]BF_4$ wherein nbd is norbornadiene, and the ligand.

Hereinafter, the present invention is described in further detail. In the meantime, "n" means normal, "i", means iso, "s" means secondary, "t" means tertiary, "c" means cyclo, "o" means ortho, "m" means meta, "p" means para, "Me" means methyl group, "Et" means ethyl group, "Ph" means phenyl group, "Ac" means acetyl group, "Ts" means paratoluenesulfonyl group, "Boc" means tertiary butoxy carbonyl group, "cod" means 1,5-cyclooctadiene and "nbd" means norbornadiene in this specification.

First of all, each substituent of substituents $R^1$ and $R^2$ is described.

Halogen atom includes fluorine atom, chlorine atom, bromine atom and iodine atom.

$C_{1-4}$ alkyl group may be a straight-chain alkyl group or branched alkyl group, or contain $C_{3-4}$ cycloalkyl group, and includes for example methyl group, ethyl group, n-propyl group, i-propyl group, c-propyl group, n-butyl group, i-butyl group, s-butyl group, t-butyl group, c-butyl group, 1-methyl-c-propyl group and 2-methyl-c-propyl group, etc.

$C_{1-6}$ alkyl group may be a straight-chain alkyl group or branched alkyl group, or contain $C_{3-6}$ cycloalkyl group, and includes for example in addition to the above-mentioned groups, n-pentyl group, 1-methyl-n-butyl group, 2-methyl-n-butyl group, 3-methyl-n-butyl group, 1,1-dimethyl-n-propyl group, 1,2-dimethyl-n-propyl group, 2,2-dimethyl-n-propyl group, 1-ethyl-n-propyl group, c-pentyl group, 1-methyl-c-butyl group, 2-methyl-c-butyl group, 3-methyl-c-butyl group, 1,2-dimethyl-α-propyl group, 2,3-dimethyl-α-propyl group, 1-ethyl-α-propyl group, 2-ethyl-α-propyl group, n-hexyl group, 1-methyl-n-pentyl group, 2-methyl-n-pentyl group, 3-methyl-n-pentyl group, 4-methyl-n-pentyl group, 1,1-dimethyl-n-butyl group, 1,2-dimethyl-n-butyl group, 1,3-dimethyl-n-butyl group, 2,2-dimethyl-n-butyl group, 2,3-dimethyl-n-butyl group, 3,3-dimethyl-n-butyl group, 1-ethyl-n-butyl group, 2-ethyl-n-butyl group, 1,1,2-trimethyl-n-propyl group, 1,2,2-trimethyl-n-propyl group, 1-ethyl-1-methyl-n-propyl group, 1-ethyl-2-methyl-n-propyl group, α-hexyl group, 1-methyl-α-pentyl group, 2-methyl-α-pentyl group, 3-methyl-c-pentyl group, 1-ethyl-c-butyl group, 2-ethyl-c-butyl group, 3-ethyl-c-butyl group, 1,2-dimethyl-c-butyl group, 1,3-dimethyl-c-butyl group, 2,2-dimethyl-c-butyl group, 2,3-dimethyl-c-butyl group, 2,4-dimethyl-c-butyl group, 3,3-dimethyl-c-butyl group, 1-n-propyl-c-propyl group, 2-n-propyl-c-propyl group, 1-i-propyl-c-propyl group, 2-i-propyl-c-propyl group, 1,2,2-trimethyl-c-propyl group, 1,2,3-trimethyl-c-propyl group, 2,2,3-trimethyl-c-propyl group, 1-ethyl-2-methyl-c-propyl group, 2-ethyl-1-methyl-c-propyl group, 2-ethyl-2-methyl-c-propyl group and 2-ethyl-3-methyl-c-propyl group, etc.

$C_{1-7}$ alkyl group may be a straight-chain alkyl group or branched alkyl group, or contain $C_{3-7}$ cycloalkyl group, and includes for example in addition to the above-mentioned groups, 1-heptyl group, 2-heptyl group, c-heptyl group, 1-ethyl-1,2-dimethyl-n-propyl group and 1-ethyl-2,2-dimethyl-n-propyl group, etc.

$C_{1-20}$ alkyl group may be a straight-chain alkyl group or branched alkyl group, or contain $C_{3-20}$ cycloalkyl group, and includes in addition to the above-mentioned groups, 1-methyl-1-ethyl-n-pentyl group, 1-octyl group, 3-octyl group, c-octyl group, 4-methyl-3-n-heptyl group, 8-methyl-2-n-heptyl group, 2-propyl-1-n-heptyl group, 2,4,4-trimethyl-1-n-pentyl group, 1-nonyl group, 2-nonyl group, 2,6-dimethyl-4-n-heptyl group, 3-ethyl-2,2-dimethyl-3-n-pentyl group, 3,5,5-trimethyl-1-n-hexyl group, 1-decyl group, 2-decyl group, 4-decyl group, 3,7-dimethyl-1-n-octyl group, 3,7-dimethyl-3-n-octyl group, n-undecyl group, n-dodecyl group, n-tridecyl group, n-tetradecyl group, n-pentadecyl group, n-hexadecyl group, n-heptadecyl group, n-octadecyl group, n-nonadecyl group and n-eicosyl, etc.

$C_{1-4}$ alkoxy group may be a straight-chain alkoxy group or branched alkoxy group, or contain $C_{3-4}$ cycloalkoxy group, and includes methoxy group, ethoxy group, n-propoxy group, i-propoxy group, c-propoxy group, n-butoxy group, i-butoxy group, s-butoxy group, t-butoxy group, c-butoxy group, 1-methyl-c-propoxy group and 2-methyl-c-propoxy group, etc.

$C_{1-6}$ alkoxy group may be a straight-chain alkoxy group or branched alkoxy group, or contain $C_{3-6}$ cycloalkoxy group, and includes in addition to the above-mentioned groups, n-pentyloxy group, 1-methyl-n-butoxy group, 2-methyl-n-butoxy group, 3-methyl-n-butoxy group, 1,1-dimethyl-n-propoxy group, 1,2-dimethyl-n-propoxy group, 2,2-dimethyl-n-propoxy group, 1 ethyl-n-propoxy group, c-pentyloxy group, 1-methyl-c-butoxy group, 2-methyl-c-butoxy group, 3-methyl-c-butoxy group, 1,2-dimethyl-c-propoxy group, 2,3-dimethyl-c-propoxy group, 1 ethyl-c-propoxy group, 2-ethyl-c-propoxy group, n-hexyloxy group, 1-methyl-n-pentyloxy group, 2-methyl-n-pentyloxy group, 3-methyl-n-pentyloxy group, 4-methyl-n-pentyloxy group, 1,1-dimethyl-n-butoxy group, 1,2-dimethyl-n-butoxy group, 1,3-dimethyl-n-butoxy group, 2,2-dimethyl-n-butoxy group, 2,3-dimethyl-n-butoxy group, 3,3-dimethyl-n-butoxy group, 1-ethyl-n-butoxy group, 2-ethyl-n-butoxy group, 1,1,2-trimethyl-n-propoxy group, 1,2,2-trimethyl-n-propoxy group, 1-ethyl-1-methyl-n-propoxy group, 1-ethyl-2-methyl-n-propoxy group, c-hexyloxy group, 1-methyl-c-pentyloxy group, 2-methyl-c-pentyloxy group, 3-methyl-c-pentyloxy group, 1-ethyl-c-butoxy group, 2-ethyl-c-butoxy group, 3-ethyl-c-butoxy group, 1,2-dimethyl-c-butoxy group, 1,3-dimethyl-c-butoxy group, 2,2-dimethyl-c-butoxy group, 2,3-dimethyl-c-butoxy group, 2,4-dimethyl-c-butoxy group, 3,3-dimethyl-c-butoxy group, 1-n-propyl-c-propoxy group, 2-n-propyl-c-propoxy group, 1-i-propyl-c-propoxy group, 2-i-propyl-c-propoxy group, 1,2,2-trimethyl-c-propoxy group, 1,2,3-trimethyl-c-propoxy group, 2,2,3-trimethyl-c-propoxy group, 1-ethyl-2-methyl-c-propoxy group, 2-ethyl-1-methyl-c-propoxy group, 2-ethyl-2-methyl-c-propoxy group and 2-ethyl-3-methyl-c-propoxy group, etc.

$C_{1-6}$ alkoxycarbonyl group may be a straight-chain or branched alkoxycarbonyl group, or contain $C_{3-6}$ cycloalkoxycarbonyl group, and includes methoxycarbonyl group, ethoxycarbonyl group, n-propoxycarbonyl group, i-propoxycarbonyl group, c-propoxycarbonyl group, n-butoxycarbonyl group, i-butoxycarbonyl group, s-butoxycarbonyl group, t-butoxycarbonyl group, c-butoxycarbonyl group, 1-methyl-c-propoxycarbonyl group, 2-methyl-c-propoxycarbonyl group, n-pentyloxycarbonyl group, 1-methyl-n-butoxycarbonyl group, 2-methyl-n-butoxycarbonyl group, 3-methyl-n-butoxycarbonyl group, 1,1-dimethyl-n-propoxycarbonyl group, 1,2-dimethyl-n-propoxycarbonyl group, 2,2-dimethyl-n-propoxycarbonyl group, 1-ethyl-n-propoxycarbonyl group, c-pentyloxycarbonyl group, 1-methyl-c-butoxycarbonyl group, 2-methyl-c-butoxycarbonyl group, 3-methyl-c-butoxycarbonyl group, 1,2-dimethyl-c-propoxycarbonyl group, 2,3-dimethyl-c-propoxycarbonyl group, 1-ethyl-c-propoxycarbonyl group, 2-ethyl-propoxycarbonyl group, n-hexyloxycarbonyl group, 1-methyl-n-pentyloxycarbonyl group, 2-methyl-n-pentyloxycarbonyl group, 3-methyl-n-pentyloxycarbonyl group, 4-methyl-n-pentyloxycarbonyl group, 1,1-dimethyl-n-butoxycarbonyl group, 1,2-dimethyl-n-butoxycarbonyl group, 1,3-dimethyl-n-butoxycarbonyl group, 2,2-dimethyl-n-butoxycarbonyl group, 2,3-dimethyl-n-butoxycarbonyl group, 3,3-dimethyl-n-butoxycarbonyl group, 1-ethyl-n-butoxycarbonyl group, 2-ethyl-n-butoxycarbonyl group, 1,1,2-trimethyl-n-propoxycarbonyl group, 1,2,2-trimethyl-n-propoxycarbonyl group, 1-ethyl-1-methyl-n-propoxycarbonyl group, 1-ethyl-2-methyl-n-propoxycarbonyl group, c-hexyloxycarbonyl group, 1-methyl-c-pentyloxycarbonyl group, 2-methyl-c-pentyloxycarbonyl group, 3-methyl-c-pentyloxycarbonyl group, 1-ethyl-c-butoxycarbonyl group, 2-ethyl-c-butoxycarbonyl group, 3-ethyl-c-butoxycarbonyl group, 1,2-dimethyl-c-butoxycarbonyl group, 1,3-dimethyl-c-butoxycarbonyl group, 2,2-dimethyl-c-butoxycarbonyl group, 2,3-dimethyl-c-butoxycarbonyl group, 2,4-dimethyl-c-butoxycarbonyl group, 3,3-dimethyl-c-butoxycarbonyl group, 1-n-propyl-c-propoxycarbonyl group, 2-n-propyl-c-propoxycarbonyl group, 1-i-propyl-c-propoxycarbonyl group, 2-i-propyl-c-propoxycarbonyl group, 1,2,2-trimethyl-c-propoxycarbonyl group, 1,2,3-trimethyl-c-propoxycarbonyl group, 2,2,3-trimethyl-c-propoxycarbonyl group, 1-ethyl-2-methyl-c-propoxycarbonyl group, 2-ethyl-1-methyl-c-propoxycarbonyl group, 2-ethyl-2-methyl-c-propoxycarbonyl group and 2-ethyl-3-methyl-c-propoxycarbonyl group, etc.

$C_{1-6}$ alkylcarbonyloxy group may be a straight-chain or branched alkylcarbonyloxy group, or contain $C_{3-6}$ cycloalkylcarbonyloxy group, and includes methylcarbonyloxy group, ethylcarbonyloxy group, n-propylcarbonyloxy group, i-propylcarbonyloxy group, c-propylcarbonyloxy group, n-butylcarbonyloxy group, i-butylcarbonyloxy group, s-butylcarbonyloxy group, t-butylcarbonyloxy group, c-butylcarbonyloxy group, 1-methyl-c-propylcarbonyloxy group, 2-methyl-c-propylcarbonyloxy group, n-pentylcarbonyloxy group, 1-methyl-n-butylcarbonyloxy group, 2-methyl-n-butylcarbonyloxy group, 3-methyl-n-butylcarbonyloxy group, 1,1-dimethyl-n-propylcarbonyloxy group, 1,2-dimethyl-n-propylcarbonyloxy group, 2,2-dimethyl-n-propylcarbonyloxy group, 1-ethyl-n-propylcarbonyloxy group, c-pentylcarbonyloxy group, 1-methyl-n-butylcarbonyloxy group, 2-methyl-c-butylcarbonyloxy group, 3-methyl-c-butylcarbonyloxy group, 1,2-dimethyl-c-propylcarbonyloxy group, 2,3-dimethyl-c-propylcarbonyloxy group, 1-ethyl-c-propylcarbonyloxy group, 2-ethyl-c-propylcarbonyloxy group, n-hexylcarbonyloxy group, 1-methyl-n-pentylcarbonyloxy group, 2-methyl-n-pentylcarbonyloxy group, 3-methyl-n-pentylcarbonyloxy group, 4-methyl-n-pentylcarbonyloxy group, 1,1-dimethyl-n-butylcarbonyloxy group, 1,2-dimethyl-n-butylcarbonyloxy group, 1,3-dimethyl-n-butylcarbonyloxy group, 2,2-dimethyl-n-butylcarbonyloxy group, 2,3-dimethyl-n-butylcarbonyloxy group, 3,3-dimethyl-n-butylcarbonyloxy group, 1-ethyl-n-butylcarbonyloxy group, 2-ethyl-n-butylcarbonyloxy group, 1,1,2-trimethyl-n-propylcarbonyloxy group, 1,2,2-trimethyl-n-propylcarbonyloxy group, 1-ethyl-1-methyl-n-propylcarbonyloxy group, 1-ethyl-2-methyl-n-propylcarbonyloxy group, c-hexylcarbonyloxy group, 1-methyl-c-pentylcarbonyloxy group, 2-methyl-c-pentylcarbonyloxy group, 3-methyl-c-pentylcarbonyloxy group, 1-ethyl-c-butylcarbonyloxy group, 2-ethyl-c-butylcarbonyloxy group, 3-ethyl-c-butylcarbonyloxy group, 1,2-dimethyl-c-butylcarbonyloxy group, 1,3-dimethyl-c-butylcarbonyloxy group, 2,2-dimethyl-c-butylcarbonyloxy group, 2,3-dimethyl-c-butylcarbonyloxy group, 2,4-dimethyl-c-butylcarbonyloxy group, 3,3-dimethyl-c-butylcarbonyloxy group, 1-n-propyl-c-propylcarbonyloxy group, 2-n-propyl-c-propylcarbonyloxy group, 1-i-propyl-c-propylcarbonyloxy group, 2-i-propyl-c-propylcarbonyloxy group, 1,2,2-trimethyl-c-propylcarbonyloxy group, 1,2,3-trimethyl-c-propylcarbonyloxy group, 2,2,3-trimethyl-c-propylcarbonyloxy group, 1-ethyl-2-methyl-c-propylcarbonyloxy group, 2-ethyl-1-methyl-c-propylcarbonyloxy group, 2-ethyl-2-methyl-c-propylcarbonyloxy group and 2-ethyl-3-methyl-c-propylcarbonyloxy group, etc.

$C_{4-12}$ aromatic group includes 2-furyl group, 3-furyl group, 2-thienyl group, 3-thienyl group, phenyl group, α-naphthyl group, β-naphthyl group, o-biphenylyl group, m-biphenylyl group and p-biphenylyl group, etc.

Next, specific examples of each substituent of $R^1$ and $R^2$ are described.

Specific examples of $R^1$ include methyl group, ethyl group, h-propyl group, i-propyl group, c-propyl group, n-butyl group, i-butyl group, s-butyl group, t-butyl group, c-butyl group, 1-methyl-c-propyl group, 2-methyl-c-propyl group, n-pentyl group, 1-methyl-n-butyl group, 2-methyl-n-butyl group, 3-methyl-n-butyl group, 1,1-dimethyl-n-propyl group, 1,2-dimethyl-n-propyl group, 2,2-dimethyl-n-propyl group, 1-ethyl-n-propyl group, c-pentyl group, 1-methyl-c-butyl group, 2-methyl-c-butyl group, 3-methyl-c-butyl group, 1,2-dimethyl-c-propyl group, 2,3-dimethyl-c-propyl group, 1-ethyl-c-propyl group, 2-ethyl-c-propyl group, n-hexyl group, 1-methyl-n-pentyl group, 2-methyl-n-pentyl group, 3-methyl-n-pentyl group, 4-methyl-n-pentyl group, 1,1-dimethyl-n-butyl group, 1,2-dimethyl-n-butyl group, 1,3-dimethyl-n-butyl group, 2,2-dimethyl-n-butyl group, 2,3-dimethyl-n-butyl group, 3,3-dimethyl-n-butyl group, 1-ethyl-n-butyl group, 2-ethyl-n-butyl group, 1,1,2-trimethyl-n-propyl group, 1,2,2-trimethyl-n-propyl group, 1-ethyl-1-methyl-n-propyl group, 1-ethyl-2-methyl-n-propyl group, c-hexyl group, 1-methyl-c-pentyl group, 2-methyl-c-pentyl group, 3-methyl-c-pentyl group, 1-ethyl-c-butyl group, 2-ethyl-c-butyl group, 3-ethyl-c-butyl group, 1,2-dimethyl-c-butyl group, 1,3-dimethyl-c-butyl group, 2,2-dimethyl-c-butyl group, 2,3-dimethyl-c-butyl group, 2,4-dimethyl-c-butyl group, 3,3-dimethyl-c-butyl group, 1-n-propyl-c-propyl group, 2-n-propyl-c-propyl group, 1-i-propyl-c-propyl group, 2-i-propyl-c-propyl group, 1,2,2-trimethyl-c-propyl group, 1,2,3-trimethyl-c-propyl group, 2,2,3-trimethyl-c-propyl group, 1-ethyl-2-methyl-c-propyl group, 2-ethyl-1-methyl-c-propyl group, 2-ethyl-2-methyl-c-propyl group, 2-ethyl-3-methyl-c-propyl group, c-heptyl group, c-octyl group, 2-furyl group, 3-furyl group, 2-thienyl group, 3-thienyl group, phenyl group, o-methylphenyl group, m-methylphenyl group, p-methylphenyl group, o-methoxyphenyl group, m-methoxyphenyl group, p-methoxyphenyl group, o-benzyloxyphenyl group, m-benzyloxyphenyl group, p-benzyloxyphenyl group, o-chlorophenyl group, m-chlorophenyl group, p-chlorophenyl group, o-bromophenyl group, m-bromophenyl group, p-bromophenyl group, 3,4-methylene dioxyphenyl group, α-naphthyl group, β-naphthyl group and benzyl group etc., and particularly n-propyl group, i-propyl group, t-butyl group, c-pentyl group, c-hexyl group, c-heptyl group, phenyl group, p-benzyloxyphenyl group, m-methylphenyl group, p-methylphenyl group, β-naphthyl group, p-bromophenyl group, 3,4-methylene dioxyphenyl group, 2-thienyl group and 2-furyl group, and further phenyl group, p-benzyloxyphenyl group, p-bromophenyl group, 3,4-methylene dioxyphenyl group, 2-thienyl group and 2-furyl group.

Specific examples of $R^2$ include methyl group, ethyl group, n-propyl group, i-propyl group, c-propyl group, n-butyl group, i-butyl group, s-butyl group, t-butyl group, c-butyl group, 1-methyl-c-propyl group, 2-methyl-c-propyl group, n-pentyl group, 1-methyl-n-butyl group, 2-methyl-n-butyl group, 3-methyl-n-butyl group, 1,1-dimethyl-n-propyl group, 1,2-dimethyl-n-propyl group, 2,2-dimethyl-n-propyl group, 1-ethyl-n-propyl group, c-pentyl group, 1-methyl-c-butyl group, 2-methyl-c-butyl group, 3-methyl-c-butyl group, 1,2-dimethyl-c-propyl group, 2,3-dimethyl-c-propyl group, 1-ethyl-c-propyl group, 2-ethyl-c-propyl group, n-hexyl group, 1-methyl-n-pentyl group, 2-methyl-n-pentyl group, 3-methyl-n-pentyl group, 4-methyl-n-pentyl group, 1,1-dimethyl-n-butyl group, 1,2-dimethyl-n-butyl group, 1,3-dimethyl-n-butyl group, 2,2-dimethyl-n-butyl group, 2,3-dimethyl-n-butyl group, 3,3-dimethyl-n-butyl group, 1-ethyl-n-butyl group, 2-ethyl-n-butyl group, 1,1,2-trimethyl-n-propyl group, 1,2,2-trimethyl-n-propyl group, 1-ethyl-1-methyl-n-propyl group, 1-ethyl-2-methyl-n-propyl group, c-hexyl group, 1-methyl-c-pentyl group, 2-methyl-c-pentyl group, 3-methyl-c-pentyl group, 1-ethyl-c-butyl group, 2-ethyl-c-butyl group, 3-ethyl-c-butyl group, 1,2-dimethyl-c-butyl group, 1,3-dimethyl-c-butyl group, 2,2-dimethyl-c-butyl group, 2,3-dimethyl-c-butyl group, 2,4-dimethyl-c-butyl group, 3,3-dimethyl-c-butyl group, 1-n-propyl-c-propyl group, 2-n-propyl-c-propyl group, 1-i-propyl-c-propyl group, 2-i-propyl-c-propyl group, 1,2,2-trimethyl-c-propyl group, 1,2,3-trimethyl-c-propyl group, 2,2,3-trimethyl-c-propyl group, 1-ethyl-2-methyl-c-propyl group, 2-ethyl-1-methyl-c-propyl group, 2-ethyl-2-methyl-c-propyl group, 2-ethyl-3-methyl-c-propyl group, c-heptyl group, c-octyl group, phenyl group and benzyl group etc., and particularly methyl group, ethyl group and benzyl group.

Preferable α-aminoacyl acetic acid ester compounds of formula (1) include the following:

1) α-aminoacyl acetic acid ester compounds of formula (1) wherein $R^1$ is $C_{1-20}$ alkyl group or $C_{4-12}$ aromatic group (the aromatic group may be arbitrarily substituted with halogen atom, $C_{1-6}$ alkyl group, $C_{1-6}$ alkoxy group or benzyloxy group);

2) α-aminoacyl acetic acid ester compounds of formula (1) wherein $R^2$ is $C_{1-6}$ alkyl group, or $C_{1-6}$ alkyl group substituted with $C_{4-12}$ aromatic group;

3) α-aminoacyl acetic acid ester compounds of formula (1) wherein $R^1$ is $C_{1-20}$ alkyl group or $C_{4-12}$ aromatic group (the aromatic group may be arbitrarily substituted with halogen atom, $C_{1-6}$ alkyl group, $C_{1-6}$ alkoxy group or benzyloxy group), and $R^2$ is $C_{1-6}$ alkyl group, or $C_{1-6}$ alkyl group substituted with $C_{4-12}$ aromatic group;

4) α-aminoacyl acetic acid ester compounds of formula (1) wherein $R^1$ is n-propyl group, i-propyl group, t-butyl group, c-pentyl group, c-hexyl group, c-heptyl group, phenyl group, p-benzyloxyphenyl group, m-methylphenyl group, p-methylphenyl group, β-naphthyl group, p-bromophenyl group, 3,4-methylene dioxyphenyl group, 2-thienyl group or 2-furyl group;

5) α-aminoacyl acetic acid ester compounds of formula (1) wherein $R^2$ is methyl group, ethyl group or benzyl group;

6) α-aminoacyl acetic acid ester compounds of formula (1) wherein $R^1$ is n-propyl group, i-propyl group, t-butyl group, c-pentyl group, c-hexyl group, c-heptyl group, phenyl group, p-benzyloxyphenyl group, m-methylphenyl group, p-methylphenyl group, β-naphthyl group, p-bromophenyl group, 3,4-methylene dioxyphenyl group, 2-thienyl group or 2-furyl group, and $R^2$ is methyl group, ethyl group or benzyl group; and 7) α-aminoacyl acetic acid ester compounds of formula (1) wherein $R^1$ is phenyl group, p-benzyloxyphenyl group, p-bromophenyl group, 3,4-methylene dioxyphenyl group, 2-thienyl group or 2-furyl group, and $R^2$ is methyl group, ethyl group or benzyl group.

Preferable optically active compounds of formula (4) or (4') include the following:

1) compounds wherein $R^3$ is phenyl group, cyclohexyl group, 2-furyl group, 3,5-bistrifluoromethylphenyl group, 4-trifluoromethylphenyl group or 3,5-dimethyl-4-methoxyphenyl group, and $R^4$ is tert-butyl group, cyclohexyl group, phenyl group or 3,5-dimethylphenyl group;

2) compound that is (R)-(−)-1-[(S)-2-(bis(4-trifluoromethylphenyl)phosphino)ferrocenyl]ethyl-di-tert-butylphosphine, (R)-(−)-1-[(S)-2-(di(3,5-bistrifluoromethylphenyl)phosphino)ferrocenyl]ethyl-dicyclohexylphosphine, (R)-(−)-1-[(S)-2-(di(3,5-bistrifluoromethylphenyl)phosphino)ferrocenyl]ethyl-di(3,5-dimethylphenyl)phosphine, (R)-(−)-1-[(S)-2-(dicyclohexylphosphino)ferrocenyl]ethyl-di-tert-butylphosphine, (R)-(−)-1-(S)-2-(dicyclohexylphosphino)ferrocenyl]ethyl-dicyclohexylphosphine, (S)-(+)-1-[(R)-2-(dicyclohexylphosphino)ferrocenyl]ethyl-dicyclohexylphosphine, (S)-(+)-1-[(R)-2-(dicyclohexylphosphino)ferrocenyl]ethyl-diphenylphosphine, (R)-(−)-1-[(S)-2-(bis(3,5-dimethyl-4-methoxyphenyl) phosphino)ferrocenyl]ethyl-dicyclohexylphosphine, (S)-(+)-1-[(R)-2-(di-2-furylphosphino)ferrocenyl]ethyl-di(3,5-dimethylphenyl) phosphine, (R)-(−)-1-[(S)-2-(diphenylphosphino) ferrocenyl]ethyl-di-tert-butylphosphine, (S)-(+)-1-[(R)-2-(diphenylphosphino)ferrocenyl]ethyl-di-tert-butylphosphine, (R)-(−)-1-(R)-2-(diphenylphosphino) ferrocenyl]ethyl-dicyclohexylphosphine, (S)-(+)-1-[(R)-2-(diphenylphosphino)ferrocenyl]ethyl-dicyclohexylphosphine, (R)-(−)-1-[(S)-2-(dicyclohexylphosphino)ferrocenyl]ethyl-diphenylphosphine or (R)-(−)-1-[(S)-2-(diphenylphosphino) ferrocenyl]ethyl-di(3,5-dimethylphenyl)phosphine;

3) compound that is (R)-(−)-1-[(S)-2-(diphenylphosphino) ferrocenyl]ethyl-di-tert-butylphosphine.

In the meantime, as the optically active compound of formula (4) or (4'), commercially available one can be used, and also the compounds prepared with reference to the production process disclosed in EP-A-0612758 (1994) can be used.

Preferable optically active compounds of formula (5) include the following:

1) compounds wherein $R^6$ is cyclohexyl group, phenyl group, 4-methylphenyl group, 4-methoxyphenyl group or 4-tert-butylphenyl group, $R^7$ is methyl group or methoxy group, $R^8$ is hydrogen atom or methoxy group, and $R^9$ is hydrogen atom, methyl group or dimethylamino group;

2) compound that is 2,2'-dimethyl-6,6'-bis(diphenylphosphino)-1,1'-biphenyl, 2,2'-dimethyl-6,6'-bis(dicyclohexylphosphino)-1,1'-biphenyl, 2,2'-dimethyl-4,4'-bis(dimethylamino)-6,6'-bis(diphenylphosphino)-1,1'-biphenyl, 2,2',4,4'-tetramethyl-6,6'-bis(diphenylphosphino)-1,1'-biphenyl, 2,2'-dimethoxy-6,6'-bis(diphenylphosphino)-1,1'-biphenyl, 2,2',3,3'-tetramethoxy-6,6'-bis(diphenylphosphino)-1,1'-biphenyl, 2,2',4,4'-tetramethyl-3,3'-dimethoxy-6,6'-bis(diphenylphosphino)-1,1'-biphenyl, 2,2'-dimethyl-6,6'-bis(di-4-methylphenylphosphino)-1,1'-biphenyl, 2,2'-dimethyl-6,6'-bis(di-4-tert-butylphenylphosphino)-1,1'-biphenyl or 2,2',4,4'-tetramethyl-3,3'-dimethoxy-6,6'-bis(di-4-methoxyphenylphosphino)-1,1'-biphenyl;

3) compound that is 2,2'-dimethoxy-6,6'-bis(diphenylphosphino)-1,1'-biphenyl.

In the meantime, as the optically active compound of formula (5), commercially available one can be used, and also the compounds stated in publications can be used (see, for example R. Noyori ed. Asymmetric Catalysis in Organic Synthesis, (1994) Jhon Wiley & Sons, Inc, New York).

The rhodium complex (catalyst) used for the catalytic asymmetric hydrogenation in the present invention can be prepared from a rhodium agent and a ligand (an optically active compound), and optionally an additive that can be coordinated.

The rhodium agent includes di-μ-chlorotetrakis(cyclooctene) 2rhodium, di-μ-chlorobis(1,5-cyclooctadiene) 2rhodium and 1,5-cyclooctadienebis(acetonitrile) rhodium tetrafluoroborate, $[Rh(nbd)_2]BF_4$, $[Rh(nbd)_2]BF_4$ and $[RhCl(nbd)]_2$, preferably $[Rh(nbd)_2]BF_4$ and $[RhCl(nbd)]_2$.

The used amount of the ligand is 1 equivalent or more, preferably 1 to 2 equivalents, more preferably 1.1 to 1.5 equivalent based on the amount of the rhodium agent.

Generally, the preparation of the rhodium complex used for catalytic asymmetric hydrogenation is preferably performed in the presence of an inert gas such as argon or the like.

BEST MODE FOR CARRYING OUT THE INVENTION

The process for producing optically active β-hydroxy-α-aminocarboxylic acid derivative of the present invention is described.

As shown in the scheme below, an optically active β-hydroxy-α-aminocarboxylic acid derivative of formula (2) or (3) can be produced by reducing an α-aminoacyl acetic acid ester compound of formula (1) with hydrogen in the presence of a catalyst (rhodium complex) used for catalytic asymmetric hydrogenation and an acid:

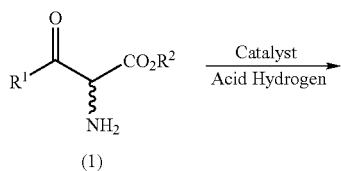

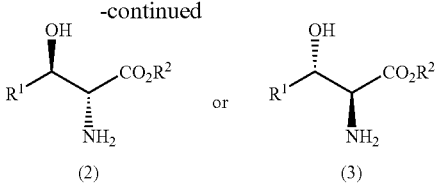

Generally, the above-mentioned reaction is carried out in a solvent. The solvent is not specifically limited so long as it does not pertain to the reaction, and includes for example halogen-type solvents such as 1,1-dichloroethane, 1,2-dichloroethane, methylene chloride, chloroform, chlorobenzene and 1,2-dichlorobenzene or the like, ether-type solvents such as diethyl ether, diisopropyl ether, tetrahydrofuran, or the like, alcohol-type solvent such as methanol, ethanol, n-propanol, i-propanol, 2-butanol, and ethylene glycol or the like, acetic acid and arbitrary mixed solvents of the above-mentioned solvents, preferably acetic acid.

The used amount of the catalyst for catalytic asymmetric hydrogenation is a range of 0.01 to 100 mol % based on the used amount of α-aminoacyl acetic acid ester compound of formula (1). It is preferably a range of 0.01 to 20 mol %, more preferably a range of 0.1 to 10 mol %, the most preferably a range of 0.3 to 5 mol % from the standpoint of reaction efficiency and cost.

Although an α-aminoacyl acetic acid ester compound of formula (1) may be added in a solution in which an acid is present, a salt previously prepared from an α-aminoacyl acetic acid ester compound of formula (1) and an acid may be added in a solution.

From the standpoint of the stability of α-aminoacyl acetic acid compounds of formula (1), it is preferable to prepare previously a salt composed of an α-aminoacyl acetic acid ester compound of formula (1) and an acid and add the salt in a solution The used acid is preferably a strong acid. The specific examples of the strong acid are HCl, HBr, $H_2SO_4$, $HClO_4$, $CH_3SO_3H$, $PhSO_3H$, TsOH (Ts means p-toluene sulfonyl group), $CF_3SO_3H$ and $CF_3CO_2H$, etc., preferably HCl and TsOH, more preferably HCl.

The used amount of the acid is a range of 0.8 to 3 mol %, preferably a range of 0.9 to 2 mol %, more preferably a range of 0.9 to 1.5 mol % based on the used amount of α-aminoacyl acetic acid ester compound of formula (1).

In the meanwhile, when a salt previously prepared from an c-aminoacyl acetic acid ester compound of formula (1) and an acid is added, the used amount of the acid means the total amount involving acids contained in the salt.

The acetic acid salt includes an alkali metal acetate such as lithium acetate, sodium acetate and potassium acetate, etc., and ammonium acetate, etc., and preferably an alkali metal acetate such as sodium acetate.

The used amount of the acetic acid salt is a range of 0.8 to 5 equivalents, preferably a range of 0.8 to 2 equivalents based on the used amount of α-aminoacyl acetic acid ester compound of formula (1).

The used hydrogen is generally hydrogen gas.

The pressure of the used hydrogen is generally a range of 1 to 150 atm, preferably a range of 10 to 150 atm, more preferably 30 to 100 atm.

The reaction can be carried out at a reaction temperature ranging from 0° C. to a boiling point of the solvent, preferably from 10° C. to 150° C., more preferably 10° C. to 50° C.

The reaction time is not necessarily determined because it varies depending on the reaction temperature, but for example a reaction time of 12 hours or more in case where the reaction temperature is 23° C. is satisfactory.

After the completion of the reaction, an aimed optically active β-hydroxy-α-aminocarboxylic acid derivative can be obtained in a form of salt by concentrating the solvent. In addition, an aimed optically active β-hydroxy-α-aminocarboxylic acid derivative can be obtained by making the reaction solution basic and extracting with a suitable solvent.

Further, an optically active β-hydroxy-α-aminocarboxylic acid derivative of formula (2) or (3) can be isolated in a high purity by purifying by distillation, recrystallization and silica gel column chromatography, etc.

Diastereo selectivity (de: selectivity of syn form and anti form) and enantio selectivity (ee) of the optically active β-hydroxy-α-aminocarboxylic acid derivative of formula (2) or (3) obtained in the present invention can be determined by performing instrumental analysis after t-butoxycarbonylation of the resulting optically active β-hydroxy-α-aminocarboxylic acid derivative.

The process of the t-butoxycarbonylation is as follows:

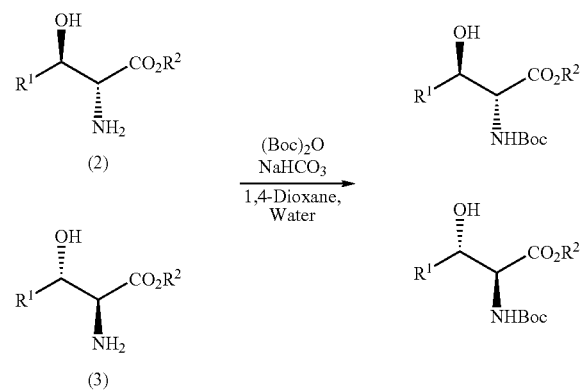

That is, the t-butoxycarbonylated compound of the optically active β-hydroxy-α-aminocarboxylic acid derivative of formula (2) or (3) can be produced by reacting the optically active β-hydroxy-α-aminocarboxylic acid derivative of formula (2) or (3) or the salt thereof with di-t-butyl dicarbonate (Boc$_2$O) in a mixed solvent of 1,4-dioxane and water in the presence of sodium hydrogen carbonate. After purification of the resulting compound by silica gel chromatography, etc., diastereo selectivity (de: selectivity of syn form and anti form) thereof can be determined with $^1$H-NMR or the like and enantio selectivity (ee) thereof can be determined with HPLC analysis or the like.

The α-aminoacyl acetic acid ester compound of formula (1) being a starting material can be produced by a process shown below.

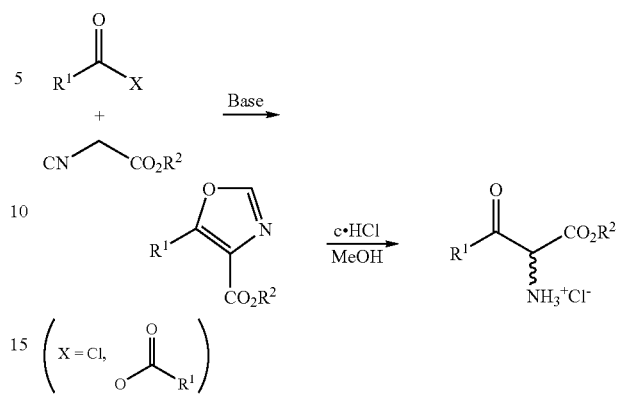

That is, the hydrochloride of the α-aminoacyl acetic acid ester compound of formula (1) can be produced by condensing an acid anhydride or acyl chloride and an isonitrile acetate in the presence of a base (the base includes triethyl amine, 1,8-diazabicyclo[5.4.0]undeca-7-ene or the like) to obtain an oxazole compound and then cleaving the oxazole ring with concentrated hydrochloric acid. The resulting hydrochloride can be used as such for the following reduction reaction, and can be processed with a base or the like to obtain the α-aminoacyl acetic acid ester compound of formula (1). In addition, in order to obtain the salt with other acid, the oxazole compound is cleft with other acid or the hydrochloride is subjected to salt exchange with other acid.

The hydrochloride of the α-aminoacyl acetic acid ester compound of formula (1) can be produced also by a process shown below:

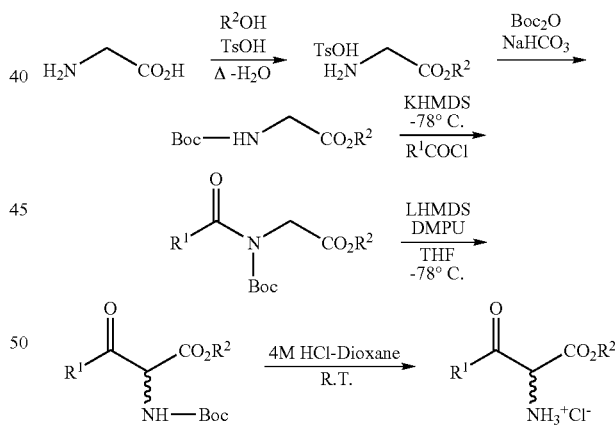

That is, the hydrochloride of the α-aminoacyl acetic acid ester compound of formula (1) can be produced by dehydrating and condensing glycine with an alcohol in the presence of TsOH (p-toluenesulfonic acid) to obtain an ester, subjecting the amino group to t-butoxycarbonylation with Boc$_2$O (di-t-butyl dicarbonate), treating with KHMDS (potassium hexamethyl disilazide), subjecting to amidation by adding acyl chloride, and carrying out rearrangement reaction by treating with LHMDS (lithium hexamethyl disilazide) and DMPU (1,3-dimethyl-3,4,5,6-perhydropyrimidine-2-one) to obtain Boc form of the α-aminoacyl acetic acid ester compound, then removing Boc with hydrochloric acid.

EXAMPLES

Hereinafter, the present invention is described based on examples to which the present invention is not limited at all.

In the meantime, (S)-MeO-BIPHEP is 2,2'-dimethoxy-6,6'-bis(diphenyl)phosphino)-1,1'-biphenyl, (R)-(S)—PPF-P$^t$Bu$_2$ is (R)-(–)-1-[(S)-2-(diphenylphosphino)ferrocenyl] ethyl-di-tert-butylphosphine, and AcONa is sodium acetate.

Reference Example 1

Production of Substrate (6 g)

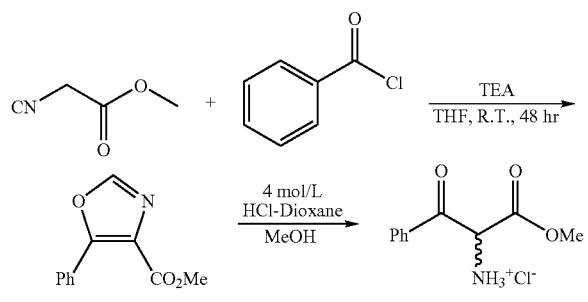

Methylisocyanoate (2.97 g. 30 mmol), benzoyl chloride (2.97 g, 30 mmol) and triethylamine (12.6 ml, 90 mmol) were added in tetrahydrofuran (50 ml), stirred at room temperature for 48 hours. Then, the solvent was distilled off under reduced pressure, ethyl acetate (100 ml) was added in the residue, and washed with water, 1 mol/L hydrochloric acid (50 ml), saturated sodium hydrogen carbonate aqueous solution (50 ml) and saturated salt water in that order. The solution was dried over anhydrous sodium sulfate, and then precipitates were filtered off, and the solvent was distilled off under reduced pressure. The residue was purified by silica gel column chromatography (100 g, ethyl acetate:n-hexane=1:5) to obtain an oxazole compound (4.07 g, 20 mmol, 67%) as colorless solid.

$^1$H-NMR (400 MHz, CDCl$_3$): δ 3.96 (s, 3H), 7.45-7.63 (3H, m, Ar—H), 7.92 (s, 1H, oxazole-H), 8.00-8.12 (2H, m, Ar—H)

FT-IRv$_{max}$ (KBr): 3108, 1717, 1582, 1651, 1516, 1495, 1433, 1354, 1325, 1312, 1221, 1195, 1109, 1087, 1068, 1010, 936, 767, 688.

The oxazole compound (2.26 g, 11.1 mmol) was dissolved in 4 mol/L hydrochloric acid-dioxane (18 ml) and methanol (18 ml), stirred at 60° C. for 24 hours. The solution was cooled to room temperature, and then concentrated. The residue was dissolved in methanol, and concentrated again. This procedure was repeated five times to perfectly remove remaining hydrochloric acid. Then, the resulting solid was washed with ether and harvested by filtration. The solid was re-crystallized from ethyl acetate and methanol to obtain Compound 6 g (1.42 g, 6.2 mmol, 56%) as colorless solid $^1$H-NMR (400 MHz, CD$_3$OD): δ 3.77 (s, 3H), 7.60 (t, J=7.6 Hz, 2H), 7.77 (t, J=7.6 Hz, 1H), 8.17 (dd, J=1.6, 8.8 Hz, 2H);

$^{13}$C-NMR (100 MHz, CD$_3$OD): δ (ppm) 54.6, 130.1, 131.0, 134.9, 136.3, 165.4, 190.0;

FABMS (NBA) m/z: 194 (M-Cl$^-$)$^+$;

FT-IRv$_{max}$ (KBr): 3441, 2840, 1739, 1688, 1597, 1274, 1217, 684.

Example 1

Production of β-Hydroxy-α-Aminocarboxylic Acid Derivative

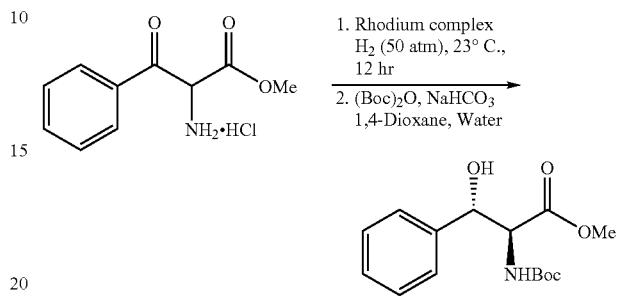

A mixture of [Rh(nbd)$_2$]BF$_4$ (2.6 mg, 0.0065 mmol) and (R)-(S)-PPF-P$^t$Bu$_2$ (4.7 mg, 0.0087 mmol) in methylene chloride (1.0 mL) was deaerated by 3-cycle freeze-thaw. Under argon atmosphere, the solution was stirred at 23° C. for 10 minutes, and then dried under reduced pressure. In the prepared rhodium catalyst, a substrate (50 mg, 0.218 mmol), sodium acetate (17.9 mg, 0.218 mmol) and acetic acid (1.1 mL) were added, and the resulting solution was deaerated by 3-cycle freeze-thaw. The resulting mixture was stirred at 23° C. for 12 hours under hydrogen pressure of 50 atm. In the reaction mixture, 3.0 mL of 1 mol/L hydrochloric acid was added, and concentrated and dried under reduced pressure at a temperature of 40° C. or less. The resulting residue was dissolved in methanol, and concentrated under reduced pressure. The procedure was repeated five times. The resulting residue was used for the next step without purification.

t-Butoxycarbonylation

In the solution of the residue obtained above in 1,4-dioxane (4 mL) and water (4 mL), Boc$_2$O (di-t-butyl dicarbonate) (52.4 mg, 0.240 mmol) and sodium hydrogen carbonate (20-2 mg, 0.240 mmol) were added at 0° C. After stirring at room temperature for 12 hours, the reaction mixture was diluted with ethyl acetate. The organic phase was washed with 1 ml/L potassium hydrogen sulfate aqueous solution, saturated sodium hydrogen carbonate aqueous solution and saturated salt water in that order, dried over anhydrous sodium sulfonate, and precipitates was filtered off and the filtrate was concentrated under reduced pressure. The resulting residue was purified by silica gel chromatography (ethyl acetate:n-hexane=1:1) to obtain N-t-butoxycarbonyl derivative (44.8 mg, 70% (2-step total), anti:syn=>95:5, 75.2% ee). HPLC analysis condition, column: CHIRALCEL OJ (Daicel Chemical Industries, Ltd.), Mobile phase: n-hexane/i-propanol=85/15, Flow rate: 0.25 mL/min., Retention time: 2S, 3S form 29.2 min., 2R, 3R form 21.9 min.

Examples 2 and 3

The procedures of Example 1 were repeated except that a condition such as a rhodium agent, a ligand, an additive, etc. was altered. Yield was shown in 2-step total.

In the meantime, the used amount of substrate:the used amount of rhodium agent:the used amount of ligand=100:3:4. In addition, the amount of additive in the table is shown in equivalent weight based on the used amount of rhodium.

TABLE 1

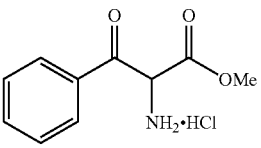

| Example No. | Rhodium agent | Ligand | Additive (equivalent weight) | Yield (%) | de (%) | ee (%) |
|---|---|---|---|---|---|---|
| 2 | [Rh(cod)$_2$]BF$_4$ | (S)-MeO-BIPHEP | AcONa (1) | 8 | >90 | 48 |
| 3 | [RhCl(nbd)]$_2$ | (R)-(S)-PPF-P$^t$Bu$_2$ | AcONa (1) | 58 | >90 | 74 |

Examples 4-11

Asymmetric hydrogenation was performed similarly to the procedures of Example 1 except that the concentration of substrate, reaction time or hydrogen pressure was altered, and then benzoylation was carried out instead of t-butoxycarbonylation, and the aimed product was isolated and yield (2-step total), de (%) and ee(%) were measured.

In the meantime, de was determined from $^1$H-NMR spectrum of the reaction mixture, and ee was determined from HPLC analysis. The HPLC analysis was performed according to the analytical condition used in Example 1.

In addition, benzoylation was performed by reacting with anhydrous benzoic acid (Bz$_2$O) in the presence of triethyl amine (TEA) in tetrahydrofuran (THF) solution.

Example 12

The procedures of Example 4 were repeated except that the substrate was altered from hydrochloride to toluene sulfonate to obtain an aimed product in a yield of 15% (2-step total), de of 92% (anti:syn=96:4) and ee of 36%.

Example 13

The procedures of Example 12 were repeated except that tetramethyl ammonium chloride was added on asymmetric hydrogenation to obtain an aimed product in a yield of 44% (2-step total), de of 88% (anti:syn=94:6) and ee of 73%.

Examples 14-18

The procedures of Example 4 were repeated except that the reaction time and substrate were variously changed.

TABLE 2

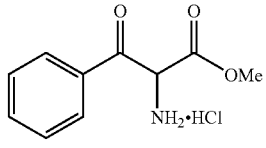

| Example No. | Substrate concentration (M) | Reaction time | Hydrogen pressure (atm) | Yield (%) | de (%) | ee (%) |
|---|---|---|---|---|---|---|
| 4 | 0.088 M | 48 hours | 50 | 71 | 83 | 73 |
| 5 | 0.044 M | 48 hours | 50 | 55 | 86 | 83 |
| 6 | 0.022 M | 48 hours | 50 | 49 | 82 | 79 |
| 7 | 0.088 M | 1 hour | 50 | 75 | 88 | 84 |
| 8 | 0.088 M | 30 minutes | 50 | 82 | 88 | 83 |
| 9 | 0.088 M | 10 minutes | 50 | 26 | 92 | 77 |
| 10 | 0.088 M | 10 minutes | 100 | 62 | 86 | 80 |
| 11 | 0.088 M | 1 hour | 5 | 34 | 86 | 80 |

In the table, BnO means benzyloxy group.

TABLE 3

1. Rh-(R)-(S)-PPF$^t$Bu$_2$ Complex H$_2$ (50 atm):
AcOH AcONa (1 equivalent)
23° C.
2. Bz$_2$O TEA THF

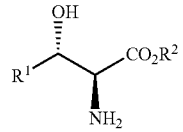

(0.088 M)

| Example No. | R | R' | Reaction time (hr) | Yield (%) | de (%) | ee (%) |
|---|---|---|---|---|---|---|
| 14 | 3,4-methylenedioxyphenyl | Et | 5 | 61 | 94 | 80 |
| 15 | 4-BnO-phenyl | Me | 3 | 53 | 84 | 84 |
| 16 | 4-Br-phenyl | Me | 2.5 | 73 | 92 | 77 |
| 17 | 2-thienyl | Et | 1.5 | 66 | 94 | 79 |
| 18 | 2-furyl | Me | 1.5 | 63 | 86 | 58 |

Comparative Example 1

The hydrogenation was performed similarly to that of Example 1 except that sodium acetate was not added to obtain an aimed product in a yield of 58%, and an optical purity of 79% ee, and a ratio of anti:syn of 56:44.

INDUSTRIAL APPLICABILITY

According to the present invention, anti forms of optically active β-hydroxy-α-aminocarboxylic acid derivatives that are useful as an intermediate for pharmaceuticals and agrochemicals can be efficiently produced.

The invention claimed is:

1. A process for producing optically active β-hydroxy-α-aminocarboxylic acid compound of formula (2) or (3)

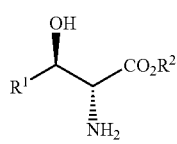

(2)

-continued (3)

wherein $R^1$ is either
  $C_{1-20}$ alkyl group wherein the $C_{1-20}$ alkyl group may be arbitrarily substituted with
    $C_{4-12}$ aromatic group that may be arbitrarily substituted with halogen atom, $C_{1-6}$ alkyl group, $C_{1-6}$ alkoxy group, $C_{1-6}$ alkoxycarbonyl group, $C_{1-6}$ alkylcarbonyloxy group or $CONR^aR^b$ wherein $R^a$ and $R^b$ are independently of each other are hydrogen atom or $C_{1-6}$ alkyl group,
    $C_{1-6}$ alkoxy group,
    $C_{1-6}$ alkoxycarbonyl group, or
    $CONR^aR^b$ wherein $R^a$ and $R^b$ are independently of each other are hydrogen atom or $C_{1-6}$ alkyl group,
  or $R^1$ is $C_{4-12}$ aromatic group that may be arbitrarily substituted with
    halogen atom,
    $C_{1-6}$ alkyl group,
    $C_{1-6}$ alkoxy group,
    $C_{1-6}$ alkoxycarbonyl group,
    $C_{1-6}$ alkylcarbonyloxy group, or
    $CONR^aR^b$ wherein $R^a$ and $R^b$ are independently of each other are hydrogen atom or $C_{1-6}$ alkyl, wherein the $C_{1-6}$ alkyl group, $C_{1-6}$ alkoxy group, $C_{1-6}$ alkoxycarbonyl group and $C_{1-6}$ alkylcarbonyloxy group may be arbitrarily substituted with $C_{4-12}$ aromatic group that may be arbitrarily substituted with halogen atom,
$R^2$ is either
  $C_{1-20}$ alkyl group wherein the $C_{1-20}$ alkyl group may be arbitrarily substituted with
    $C_{4-12}$ aromatic group that may be arbitrarily substituted with halogen atom, $C_{1-6}$ alkyl group, $C_{1-6}$ alkoxy group, $C_{1-6}$ alkoxycarbonyl group, $C_{1-6}$ alkylcarbonyloxy group or $CONR^aR^b$ wherein $R^a$ and $R^b$ are independently of each other are hydrogen atom or $C_{1-6}$ alkyl group,
    $C_{1-6}$ alkoxy group,
    $C_{1-6}$ alkoxycarbonyl group, or
    $CONR^aR^b$ wherein $R^a$ and $R^b$ are independently of each other are hydrogen atom or $C_{1-6}$ alkyl group,
  or $R^2$ is $C_{4-12}$ aromatic group that may be arbitrarily substituted with halogen atom, $C_{1-6}$ alkyl group, $C_{1-6}$ alkoxy group, $C_{1-6}$ alkoxycarbonyl group, $C_{1-6}$ alkylcarbonyloxy group or $CONR^aR^b$ wherein $R^a$ and $R^b$ are independently of each other are hydrogen atom or $C_{1-6}$ alkyl group,
the process comprising subjecting an α-aminoacyl acetic acid ester compound of formula (1)

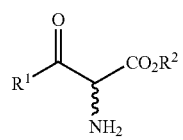

(1)

wherein $R^1$ and $R^2$ have the same meaning as the above, to hydrogenation by catalytic asymmetric hydrogenation in the presence of an acid by using as a catalyst a rhodium complex containing as a ligand an optically active compound of formula (4), (4') or (5)

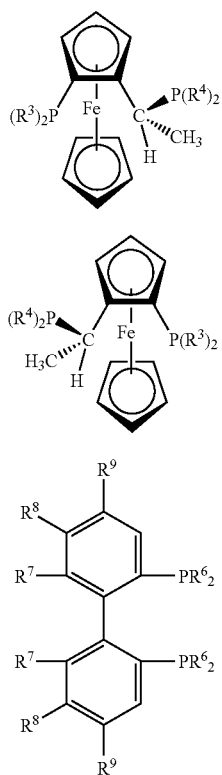

(4)

(4')

(5)

wherein $R^3$ and $R^4$ are independently of each other are
phenyl group that may be arbitrarily substituted with $C_{1-4}$ alkyl group or $C_{1-4}$ alkoxy group wherein the $C_{1-4}$ alkyl group and $C_{1-4}$ alkoxy group may be arbitrarily substituted with fluorine atom,
$C_{1-7}$ alkyl group or
2-furyl group,
$R^6$ is phenyl group, naphthyl group (the phenyl group and naphthyl group may be arbitrarily substituted with $C_{1-6}$ alkyl group or $C_{1-6}$ alkoxy group), cyclopentyl group or cyclohexyl group,
$R^7$ is methyl group or methoxy group,
$R^8$ is hydrogen atom, methyl group, methoxy group or chlorine atom, and
$R^9$ is hydrogen atom, methyl group, methoxy group, dimethylamino group or diethylamino group, and absolute configuration is either S or R,
wherein the hydrogenation is conducted in the presence of an acetic acid salt.

2. The process for producing optically active β-hydroxy-α-aminocarboxylic acid compound according to claim 1, wherein the ligand of the rhodium complex is the optically active compound of formula (4) or (4').

3. The process for producing optically active β-hydroxy-α-aminocarboxylic acid compound according to claim 2, wherein $R^3$ is phenyl group, cyclohexyl group, 2-furyl group, 3,5-bistrifluoromethylphenyl group, 4-trifluoromethylphenyl group or 3,5-dimethyl-4-methoxyphenyl group, and
$R^4$ is tert-butyl group, cyclohexyl group, phenyl group or 3,5-dimethylphenyl group.

4. The process for producing optically active β-hydroxy-α-aminocarboxylic acid compound according to claim 3, wherein the ligand is (R)-(−)-1-[(S)-2-(bis(4-trifluoromethylphenyl)phosphino)ferrocenyl]ethyl-di-tert-butylphosphine, (R)-(−)-1-[(S)-2-(di(3,5-bistrifluoromethylphenyl)phosphino)ferrocenyl]ethyl-dicyclohexylphosphine, (R)-(−)-1-[(S)-2-(di(3,5-bistrifluoromethylphenyl)phosphino)ferrocenyl]ethyl-di(3,5-dimethylphenyl)phosphine, (R)-(−)-1-[(S)-2-(dicyclohexylphosphino)ferrocenyl]ethyl-di-tert-butylphosphine, (R)-(−)-1-[(S)-2-(dicyclohexylphosphino)ferrocenyl]ethyl-dicyclohexylphosphine, (S)-(+)-1-[(R)-2-(dicyclohexylphosphino)ferrocenyl]ethyl-dicyclohexylphosphine, (S)-(+)-1-[(R)-2-(dicyclohexylphosphino)ferrocenyl]ethyl-diphenylphosphine, (R)-(−)-1-[(S)-2-(bis(3,5-dimethyl-4-methoxyphenyl)phosphino)ferrocenyl]ethyl-dicyclohexylphosphine, (S)-(+)-1-[(R)-2-(di-2-furylphosphino)ferrocenyl]ethyl-di(3,5-dimethylphenyl)phosphine, (R)-(−)-1-[(S)-2-(diphenylphosphino)ferrocenyl]ethyl-di-tert-butylphosphine, (S)-(+)-1-[(R)-2(diphenylphosphino)ferrocenyl]ethyl-di-tert-butylphosphine, (R)-(−)-1-[(R)-2-(diphenylphosphino)ferrocenyl]ethyl-dicyclohexylphosphine, (S)-(+)-1-[(R)-2-(diphenylphosphino)ferrocenyl]ethyl-dicyclohexylphosphine, (R)-(−)-1-[(S)-2-(dicyclohexylphosphino)ferrocenyl]ethyl-diphenylphosphine or (R)-(−)-1-[(S)-2-(diphenylphosphino)ferrocenyl]ethyl-di(3,5-dimethylphenyl)phosphine.

5. The process for producing optically active β-hydroxy-α-aminocarboxylic acid compound according to claim 4, wherein the ligand is (R)-(−)-1-[(S)-2-(diphenylphosphino)ferrocenyl]ethyl-di-tert-butylphosphine.

6. The process for producing optically active β-hydroxy-α-aminocarboxylic acid compound according to claim 1, wherein the ligand of the rhodium complex is the optically active compound of formula (5).

7. The process for producing optically active β-hydroxy-α-aminocarboxylic acid compound according to claim 6, wherein
$R^6$ is cyclohexyl group, phenyl group, 4-methylphenyl group, 4-methoxyphenyl group or 4-tert-butylphenyl group,
$R^7$ is methyl group or methoxy group,
$R^8$ is hydrogen atom or methoxy group, and
$R^9$ is hydrogen atom, methyl group or dimethylamino group.

8. The process for producing optically active β-hydroxy-α-aminocarboxylic acid compound according to claim 7, wherein the ligand is 2,2'-dimethyl-6,6'-bis(diphenylphosphino)-1,1'-biphenyl, 2,2'-dimethyl-6,6'-bis(dicyclohexylphosphino)-1,1'-biphenyl, 2,2'-dimethyl-4,4'-bis(dimethylamino)-6,6'-bis(diphenylphosphino)-1,1'-biphenyl, 2,2',4,4'-tetramethyl-6,6'-bis(diphenylphosphino)-1,1'-biphenyl, 2,2'-dimethoxy-6,6'-bis(diphenylphosphino)-1,1'-biphenyl, 2,2',3,3'-tetramethoxy-6,6'-bis(diphenylphosphino)-1,1'-biphenyl, 2,2',4,4'-tetramethyl-3,3'-dimethoxy-6,6'-bis(diphenylphosphino)-1,1'-biphenyl, 2,2'-dimethyl-6,6'-bis(di-4-methylphenylphosphino)-1,1'-biphenyl, 2,2'-dimethyl-6,6'-bis(di-4-tert-butylphenylphosphino)-1,1'-biphenyl or 2,2',4,4'-tetramethyl-3,3'-dimethoxy-6,6'-bis(di-4-methoxyphenylphosphino)-1,1'-biphenyl.

9. The process for producing optically active β-hydroxy-α-aminocarboxylic acid compound according to claim 8, wherein the ligand is 2,2'-dimethoxy-6,6'-bis(diphenylphosphino)-1,1'-biphenyl.

10. The process for producing optically active β-hydroxy-α-aminocarboxylic acid compound according to claim 1, wherein the acid is a strong acid.

11. The process for producing optically active β-hydroxy-α-aminocarboxylic acid compound according to claim 1, wherein acetic acid is used as a solvent.

12. The process for producing optically active β-hydroxy-α-aminocarboxylic acid compound according to claim 1, wherein the acetic acid salt is sodium acetate.

13. The process for producing optically active β-hydroxy-α-aminocarboxylic acid compound according to claim 1, wherein the rhodium complex is a compound prepared from [RhCl(nbd)]$_2$ or [Rh(nbd)$_2$]BF$_4$ wherein nbd is norbornadiene, and the ligand.

* * * * *